US00PP33601P2

(12) United States Plant Patent
Star

(10) Patent No.: US PP33,601 P2
(45) Date of Patent: Nov. 2, 2021

(54) ***SANGUISORBA* PLANT NAMED 'BIG DREAM'**

(50) Latin Name: *Sanguisorba officinalis*
Varietal Denomination: Big Dream

(71) Applicant: Jan Star, Rijnsburg (NL)

(72) Inventor: Jan Star, Rijnsburg (NL)

( * ) Notice: Subject to any disclaimer, the term of this patent is extended or adjusted under 35 U.S.C. 154(b) by 0 days.

(21) Appl. No.: 17/164,967

(22) Filed: Feb. 2, 2021

(51) Int. Cl.
*A01H 5/02* (2018.01)
*A01H 6/74* (2018.01)

(52) U.S. Cl.
USPC ..... Plt./263.1
CPC ..... *A01H 6/74* (2018.05)

(58) Field of Classification Search
USPC ..... Plt./263.1
CPC ..... A01H 5/02
See application file for complete search history.

*Primary Examiner* — Kent L Bell
(74) *Attorney, Agent, or Firm* — Penny J. Aguirre

(57) ABSTRACT

The new cultivar of *Sanguisorba* plant named 'Big Dream' that is characterized by its large inflorescences that are grey-purple in color and its stamen filaments that are grey-purple in color.

2 Drawing Sheets

Botanical classification: *Sanguisorba officinalis*.
Variety denomination: 'Big Dream'.

CROSS REFERENCE TO A RELATED APPLICATION

This application is related to a European plant breeders' rights application filed on Oct. 29, 2019, application No. 2019/2749. There have been no offers for sale anywhere in the world prior to the effective filing date of this Application and no accessibility to one of ordinary skill in the art could have been derived from the printed plant breeder's rights documents. This application is also related to U.S. Plant Patent Application filed for a plant derived from the same breeding program that is entitled *Sanguisorba* Plant Named 'Red Dream' (U.S. Plant Pat. No. 32,441).

BACKGROUND OF THE INVENTION

The present invention relates to a new and distinct cultivar of *Sanguisorba officinalis* and will be referred to hereafter by its cultivar name, 'Big Dream'. 'Big Dream' represents a new Burnet, an herbaceous perennial grown for landscape use.

The inventor discovered the new cultivar, 'Big Dream', as a chance seedling in September of 2017 in Rijnsburg, The Netherlands. The new cultivar was discovered in a production field of *Sanguisorba* 'Arnheim' (not patented) and therefore 'Arnheim' is a probable parent plant.

Asexual propagation of the new cultivar was first accomplished by division in 2017 by the inventor in Rijnsburg, The Netherlands. Asexual propagation by division has determined that the new cultivar is stable and reproduced true to type in successive generations.

SUMMARY OF THE INVENTION

The following traits have been repeatedly observed and represent the characteristics of the new cultivar. These attributes in combination distinguish 'Big Dream' as a unique cultivar of *Sanguisorba*.

1. 'Big Dream' exhibits large inflorescences that are grey-purple in color.
2. 'Big Dream' exhibits flowers with stamen filaments that are grey-purple in color.

The likely parent of 'Big Dream', 'Arnheim', is similar to 'Big Dream' in plant height and habit. 'Arnheim' differs from 'Big Dream' in having smaller inflorescences that are red in color. 'Big Dream' can be most closely compared to *Sanguisorba officinalis* cultivars 'Red Thunder' (not patented), 'Tanna' (not patented) and 'Red Dream'. All are similar to 'Big Dream' in having inflorescences that are reddish in color. 'Red Thunder' differs from 'Big Dream' in having weaker stems that are not held upright without support and inflorescences that are slightly more burgundy in color. 'Tanna' differs from 'Big Dream' in having a smaller plant height, more fern-like foliage, and inflorescences that are smaller in size and more pink-red in color. 'Red Dream' differs from 'Big Dream' in having smaller inflorescences that are more red in color, a smaller plant size, and stamen filaments that are white in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Triangle Nursery and CNB (the breeder's representative with no plant sales).

BRIEF DESCRIPTION OF THE DRAWINGS

The accompanying color photographs illustrate the overall appearance and distinct characteristics of the new *San-*

*guisorba*. The photographs were taken of a one-year-old plant of the new cultivar as field grown outdoors in Rijnsburg, The Netherlands.

Figure 1:
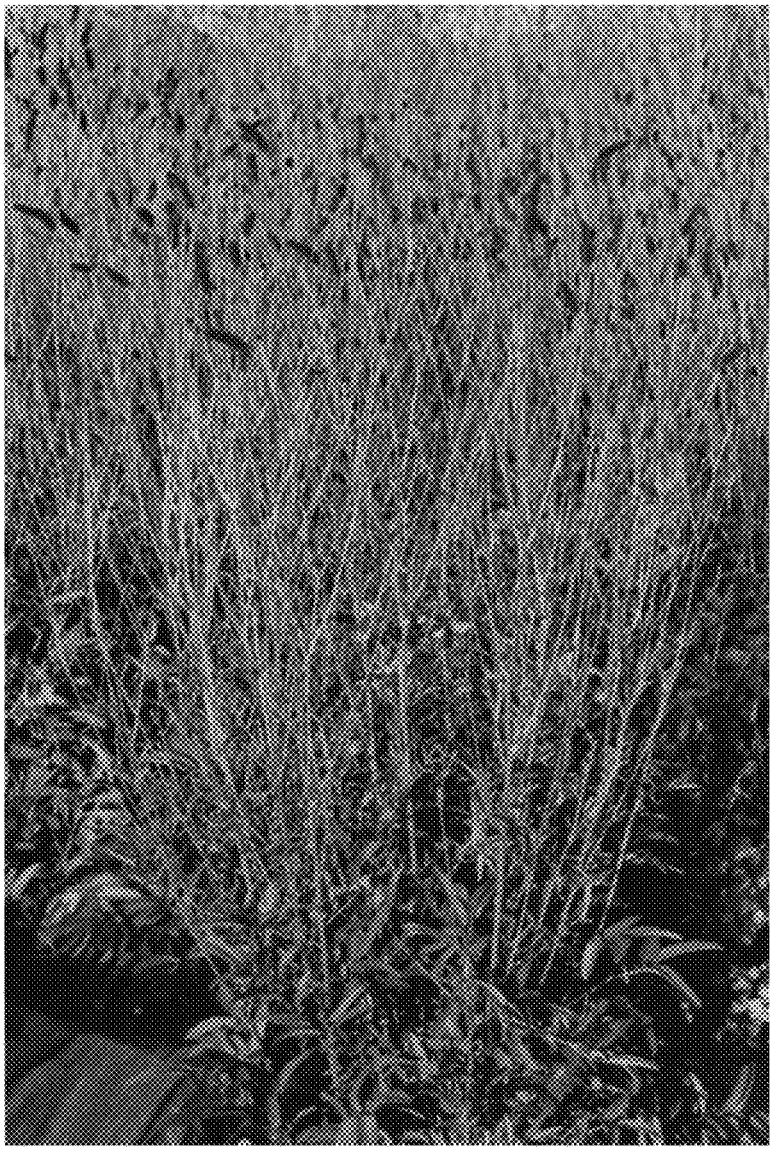

The photograph in FIG. 1 illustrates the overall habit and appearance of 'Big Dream' in bloom.

Figure 2:
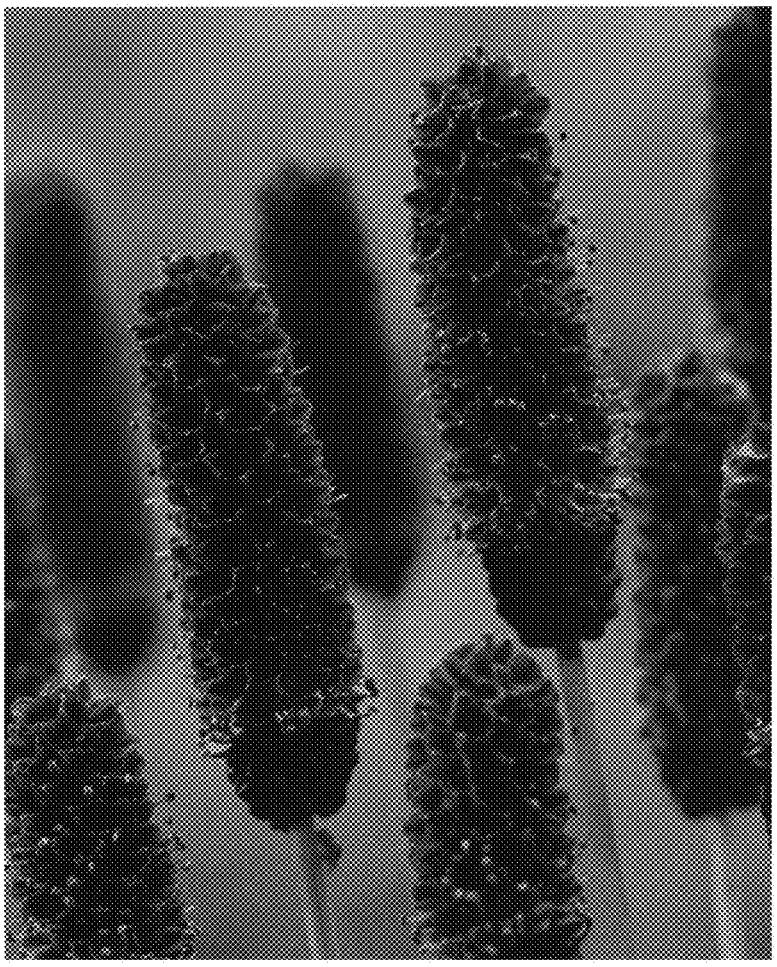

The photograph in FIG. 2 provides a close-up view of the inflorescences of 'Big Dream'.

The colors in the photographs are as close as possible with the photographic and printing technology utilized and color values cited in the detailed botanical description accurately describe the colors of the new *Sanguisorba*.

DETAILED BOTANICAL DESCRIPTION

The following is a detailed description of one-year-old plants from a division of the new cultivar as field grown in Rijnsburg, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—July through late August in The Netherlands.

*Plant habit*.—Herbaceous perennial.

*Height and spread*.—Average of 1.04 m in height from soil level to top of foliar plane, 1.65 m in height from soil level to top of floral plane, 71 cm in spread as a one-year-old field grown plant.

*Hardiness*.—At least in U.S.D.A. Zones 4 to 9.

*Diseases and pests*.—No susceptibility or resistance to diseases or pests has been observed.

*Root description*.—Moderately fibrous, very freely branched, smooth, glabrous with no root hairs, main roots are an average of 3 mm in diameter, 164C in color.

*Propagation*.—Division.

*Growth rate*.—Vigorous.

Stem description:

*Shape*.—Round, moderately angled.

*Stem color*.—Young; 144B, mature: 144B and 146D.

*Stem size*.—Up to 97.5 cm in length and 8 mm in diameter.

*Stem aspect*.—Average of 15° to vertical.

*Stem surface*.—Slightly glossy.

*Internode length*.—Up to 9.7 cm.

*Branching*.—Average of 8 basal branches, with moderate development of lateral branches; an average of 8 per plant.

Foliage description:

*Leaf shape*.—Narrow obovate.

*Leaf division*.—Compound; an average of 9 leaflets per leaf (ranges from 13 leaflets on the lower leaves to 5 leaflets on the upper leaves).

*Leaf base*.—Truncate.

*Leaf apex*.—Abruptly acute.

*Leaf aspect*.—Average of 35° to stem.

*Leaf arrangement*.—Alternate.

*Leaf size*.—Average of 35.3 cm in length (including petiole), 17.9 cm in width.

*Leaf attachment*.—Petiolate.

*Leaflet*.—Lanceolate to nearly oblong in shape, terminal leaflets; average of 8.8 cm in length, 8.3 cm in width, lateral leaflets; average of 8.3 cm in length and 2.7 cm in width, abruptly acute apex, truncate to straight base.

*Leaflet venation*.—Pinnate, upper surface color N144D, lower surface 147D.

*Leaflet margins*.—Serrate.

*Leaflet surface*.—Upper surface moderately glossy, lower surface matte.

*Leaflet color*.—Young; upper surface NN137B, lower surface 137C, mature; upper surface 137B, lower surface 138B.

*Rachis (petiole) and petiolule*.—Rachis (petiole); average of 26.4 cm in length, 3 mm in diameter, petiolule; average of 5 mm in length and 1.25 mm in diameter, moderately glossy, smooth and glabrous, strong, upper surface color 145A, petioles tinged 187A to 187B at the leaflet nodes, lower surface color between 145A and 145B.

*Stipules*.—At the base of each leaf is a leafy stipule on each side, broadly falcate to ovate in shape, 3.8 cm in length, 1.9 cm in width, surfaces smooth and glabrous, serrate margins, color upper surface NN137A, lower surface a color between 138A and 147B, at the base of each petiolule a leafy stipule is present on each side, ovate in shape, 1.5 cm in length, 1.2 cm in width, both surfaces smooth and glabrous, margins crenate, upper side moderately glossy and NN137A in color, lower side between 138A and 147B in color.

Inflorescence description:

*Type*.—Terminal spikes of numerous, densely packed flowers in elongated ovoid to oblong shaped inflorescence, determinate.

*Inflorescence size*.—Average of 4 cm in height and 1.3 cm in diameter.

*Fragrance*.—Very faint and unpleasant.

*Flower lastingness*.—About 14 days, persistent.

*Flower quantity*.—Average of 175 flowers per spike, over 20,000 flowers and buds per plant.

*Flower aspect*.—Rotate, single, outward and freely flowering.

*Flower size*.—Average of 3.5 mm in height and diameter, 4 mm in depth.

*Peduncle*.—Average of 34.5 cm in length, 3 mm in diameter, held straight up, strong, smooth and glabrous, slightly glossy, 144A in color.

*Bud description*.—Average of 2.5 mm in length, 2 mm in diameter, broadly elliptic in shape, smooth, glabrous, and matte surface, color; 187A, apex N186C, base 145D.

*Petals*.—Rotate, cruciform, average of 4, 1 row, unfused, 3 mm in length, 1.5 mm in width, ovate in shape, acute tip, cuneate base, entire margins, both surfaces glabrous, slightly velvety and matte, color; when opening upper and lower surface N186C, margined 75D, when fully open upper and lower surface 187B to 187C, tip N186C, margins N155B, base 145D, upper surface fading to 187A, margins 187C, lower surface fading to 187C, tip N186A, base 147D.

*Calyx*.—Rotate, cruciform, average of 2.5 mm in length, 3 mm in diameter.

*Sepal*.—An average of 4 in 1 row, average of 2 mm in length and 0.75 mm in width, narrow ovate in shape, acute tip, cuneate base, entire margins, both surfaces matte and moderately pubescent with short adpressed hairs; average of 0.3 mm in length and too small to measure color, color; when opening upper and lower surface N199D, fully open upper and lower surface N199D with apex N199C.

*Flower bracts*.—None.

Reproductive organs:

*Gynoecium*.—Pistil: 1, average of 2 mm in length, stigma is flattened and club-shaped, 0.4 mm in length, 0.5 mm in diameter, N186C in color, style; average of 1.25 mm in length, N186C in color, ovary; 145C in color.

*Androecium*.—Stamens; average of 4, filament; 3 mm in length, 186B, base 186D in color, anthers; broad oblong in shape, 0.5 mm in length and width, pollen; low in quantity, 16A in color.

*Fruit/seed*.—None observed.

It is claimed:

1. A new and distinct cultivar of *Sanguisorba* plant named 'Big Dream' as herein illustrated and described.

* * * * *